United States Patent
Porrata et al.

(10) Patent No.: US 7,344,511 B2
(45) Date of Patent: Mar. 18, 2008

(54) ADJUSTABLE APPARATUS AND METHOD FOR TREATING CARPAL TUNNEL SYNDROME

(75) Inventors: Humberto Luis Porrata, Fort Lauderdale, FL (US); Alejandro Alberto Porrata, Miami, FL (US)

(73) Assignee: Porrata Group LLC, Miami, FL (US)

( * ) Notice: Subject to any disclaimer, the term of this patent is extended or adjusted under 35 U.S.C. 154(b) by 688 days.

(21) Appl. No.: 10/228,739

(22) Filed: Aug. 27, 2002

(65) Prior Publication Data

US 2003/0130604 A1  Jul. 10, 2003

Related U.S. Application Data

(60) Provisional application No. 60/315,182, filed on Aug. 27, 2001.

(51) Int. Cl.
*A61F 5/00* (2006.01)
(52) U.S. Cl. .................. 602/20; 602/21; 128/878
(58) Field of Classification Search ........... 602/20–22, 602/60–64; 128/877–879
See application file for complete search history.

(56) References Cited

U.S. PATENT DOCUMENTS

| | | | |
|---|---|---|---|
| 2,388,330 A | 11/1945 | Jungmann |
| 2,823,668 A | 2/1958 | Van Court et al. |
| 2,943,859 A | 7/1960 | Koski |
| 4,067,063 A | 1/1978 | Ettinger |
| 4,378,009 A | 3/1983 | Rowley et al. |
| 4,382,439 A | 5/1983 | Shen |
| 4,479,648 A | 10/1984 | Alivo |
| 4,765,319 A | 8/1988 | Finnieston et al. |
| 4,787,376 A | 11/1988 | Eisenberg |
| 4,854,309 A | 8/1989 | Elsey |
| 4,899,763 A | 2/1990 | Sebastian |
| 4,941,460 A | 7/1990 | Working |

(Continued)

FOREIGN PATENT DOCUMENTS

DE        9200425        12/1991

(Continued)

*Primary Examiner*—Michael A. Brown
(74) *Attorney, Agent, or Firm*—Daniel A. Crowe; Allan Watts; Bryan Cave LLP

(57) ABSTRACT

The apparatus of the present invention stretches the carpal ligament and the flexor retinaculum, as well as the superficial structures and muscles of the hand, in a safe manner under precise control of the patient or a healthcare professional. Various embodiments of the inventive apparatus commonly include a housing for receiving the hypothenar portion of the patient's hand with an open side portion adapted and configured to contact and retain the hypothenar region of the patient's hand, with an edge of the housing extending along a central longitudinal dorsal portion of the hand, while a flexible resilient strap is wrapped around the thenar portion of the hand (i.e. around the thumb area) in such a manner as to pull the thenar portion of the hand upward with the edge of the housing serving as a fulcrum around which the thenar and hypothenar portions of the hand are bent. The strap is then secured to itself or to the housing to keep the thenar and hypothenar portions pulled apart during the course of treatment. The bending of the thenar and hypothenar regions of the hand around the fulcrum cause the carpal ligament and the flexor retinaculum to stretch expanding the carpal tunnel and relieving pressure on the median nerve.

12 Claims, 13 Drawing Sheets

U.S. PATENT DOCUMENTS

| | | | |
|---|---|---|---|
| 5,014,689 A | | 5/1991 | Meunchen et al. |
| 5,029,573 A | * | 7/1991 | Chow .................. 600/104 |
| 5,152,302 A | | 10/1992 | Fareed |
| 5,256,136 A | | 10/1993 | Sucher |
| 5,279,545 A | * | 1/1994 | Reese, Sr. .................. 602/21 |
| 5,297,541 A | | 3/1994 | Hensey |
| 5,366,436 A | | 11/1994 | Gibney |
| 5,385,537 A | * | 1/1995 | Davini .................. 602/21 |
| 5,405,357 A | | 4/1995 | Rowe-Lanzisera et al. |
| 5,413,553 A | | 5/1995 | Downes |
| 5,417,645 A | | 5/1995 | Lemmen |
| 5,427,577 A | | 6/1995 | Picchietti |
| 5,441,058 A | | 8/1995 | Fareed |
| 5,468,220 A | | 11/1995 | Sucher |
| 5,584,854 A | | 12/1996 | Minarik |
| 5,613,941 A | | 3/1997 | Prengler |
| 5,642,739 A | * | 7/1997 | Fareed .................. 128/881 |
| 5,647,850 A | | 7/1997 | Allen |
| 5,672,150 A | | 9/1997 | Cox |
| 5,702,355 A | | 12/1997 | Repice et al. |
| 5,707,345 A | | 1/1998 | Fulk |
| 5,810,753 A | | 9/1998 | Eberbach |
| 5,897,549 A | | 4/1999 | Tankovich |
| 5,916,185 A | | 6/1999 | Chitwood |
| 5,916,187 A | | 6/1999 | Brill |
| 5,925,007 A | | 7/1999 | Ashline |
| 5,950,628 A | | 9/1999 | Dunfee |
| 5,987,705 A | | 11/1999 | Reynolds |
| 6,029,277 A | | 2/2000 | Picchione, II |
| 6,120,472 A | | 9/2000 | Singer, Jr. |
| 6,146,347 A | * | 11/2000 | Porrata .................. 602/21 |
| 6,179,800 B1 | | 1/2001 | Torrens |
| 6,200,286 B1 | | 3/2001 | Zamani |
| 6,213,969 B1 | | 4/2001 | MacMorran et al. |
| 6,217,536 B1 | * | 4/2001 | Gustafson .................. 602/21 |
| 6,264,621 B1 | * | 7/2001 | Paske .................. 600/587 |
| 6,290,662 B1 | | 9/2001 | Morris et al. |
| 5,438,726 A1 | | 7/2003 | Porrata |
| 6,953,440 B2 | | 10/2005 | Porrata et al. |
| 2002/0072786 A1 | | 6/2002 | Gordon |
| 2003/0018286 A1 | | 1/2003 | Porrata |
| 2003/0028136 A1 | | 2/2003 | Stager |
| 2003/0125652 A1 | | 7/2003 | Porrata |
| 2003/0125690 A1 | | 7/2003 | Porrata |
| 2003/0125691 A1 | | 7/2003 | Porrata |
| 2003/0130604 A1 | | 7/2003 | Porrata |
| 2003/0130652 A1 | | 7/2003 | Porrata |
| 2003/0130690 A1 | | 7/2003 | Porrata |
| 2003/0130691 A1 | | 7/2003 | Porrata |
| 2003/0130692 A1 | | 7/2003 | Porrata |

FOREIGN PATENT DOCUMENTS

| | | |
|---|---|---|
| EP | 0 861 651 A1 | 2/1998 |
| FR | 2650175 | 12/1991 |
| WO | WO 97/23176 | 7/1997 |

* cited by examiner

ADJUSTABLE APPARATUS AND METHOD FOR TREATING CARPAL TUNNEL SYNDROME

This application claims the benefit of U.S. Provisional Application Ser. No. 60/315,182, filed Aug. 27, 2001. This application is related to four concurrently filed co-pending patent applications, namely U.S. Ser. No. 60/315,088, entitled Non-Invasive Apparatus and Method for Treating Carpal Tunnel Syndrome, U.S. Ser. No. 60/315,152, entitled Configurable Apparatus and Method for Treating Carpal Tunnel Syndrome, U.S. Ser. No. 60/315,087, entitled Adaptable Apparatus and Method for Treating Carpal Tunnel Syndrome, U.S. Ser. No. 60/315,154, entitled Automatic Apparatus and Method for Treating Carpal Tunnel Syndrome, as well as co-pending patent application U.S. Ser. No. 10/199,747, entitled Apparatus and Method for Treating Carpal Tunnel Syndrome, filed Jul. 18, 2002, the contents of which are all hereby incorporated herein by reference.

FIELD OF THE INVENTION

This invention relates generally to treatment of carpal tunnel syndrome, and more particularly to a non-invasive apparatus and method for treatment of carpal tunnel syndrome.

BACKGROUND OF THE INVENTION

Carpal tunnel syndrome is a physiological disorder that afflicts over 850,000 people each year in the United States alone. In order to better understand the cause of the carpal tunnel syndrome and the difficulty in treating this serious disorder, a detailed explanation of the physiological factors and causes of carpal tunnel syndrome is presented below. Carpal tunnel syndrome is caused by a deleterious increase in pressure on the median nerve which passes through the carpal tunnel (or canal) in the hand, adjacent to the wrist. The deleterious increase in pressure, which is commonly brought on by prolonged repetitive motion of the hand and digits, is often caused by inflammation or damage to tendons for the hand which pass through the carpal tunnel along with the median nerve. Pressure increases can also be caused by narrowing of the carpal canal and by generalized swelling of the structures in the hand. Thus, when the carpal tunnel is narrowed from ligament shortening, muscle development or structural inflammation, the median nerve is undesirably compressed.

The carpal tunnel is formed by the eight carpal bones of the hand adjacent the wrist, which bones are arranged in two rows forming a generally U-shaped inverted arch-like "tunnel" structure. The three large carpal bones of the proximal row (i.e., closest to the chest), beginning laterally (i.e., from the outside with the hand directed downward and the palm facing forward), are the scaphoid, lunate, and triquetrum; the smaller pisiform bone sits on the palmar surface of the triquetrum. The distal row, from lateral to medial, consists of the trapezium, trapezoid, capitate, and hamate carpal bones. The vault of the carpal tunnel is formed by the carpal ligament and the flexor retinaculum. Nine tendons, their tendon sheaths, and the median nerve pass through the tunnel.

The carpal ligament is made of collagen and elastin and extends from the pisiformis and hamulus of hamate bones on the ulnar aspect of the tunnel to the tubercle (i.e., projection) of trapezium and the tubercle of the scaphoid bones on the radial (i.e. lateral) aspect of the carpal tunnel. The flexor retinaculum also stretches across the carpal tunnel and attaches to, on the medial aspect of the carpal tunnel, the pisiform bone and the hook of hamate, and, on the lateral aspect, the tubercle of the scaphoid and trapezium bones. The proximal border of the flexor retinaculum corresponds generally to the transverse skin crease at the base of the hand/wrist. The carpal ligament and flexor retinaculum, along with the carpal bones, form the restricted space through which the median nerve and several tendons pass.

Symptoms of carpal tunnel syndrome include tingling sensation in the hand, discomfort, numbness, and pain localized in the hand or radiating up the arm to the shoulder. All of these symptoms can occur during the day or can make the patients wake up at night. In advanced cases, there is atrophy and weakness of the thenar area of the hand which may weaken the grip and cause objects to fall out of the hand.

Conventional treatment of carpal tunnel syndrome is divided into surgical (invasive) and conservative (non-invasive). Surgical treatment consists of making an incision on the palmar aspect of the hand and splitting the carpal ligament, thus partially opening the carpal tunnel and relieving the pressure. This procedure, while occasionally successful, often has negative consequences, which include, but are not limited to, non-resolution of symptoms often requiring a second surgery, pain in the area of the scar, and injury to the superficial palmar branch of the median nerve causing persistent neurologic symptoms such as loss of full control over the hand. Furthermore, this procedure is very expensive. Understandably, surgical treatment is often considered as a last option.

Conservative, non-invasive treatment is typically separated into three categories—mild, moderate and alternative. Mild treatments may involve the use of anti-inflammatory medications, application of resting hand splints, physical therapy, modification of patient's activities that cause the condition, and even a change in the patient's job. Moderate treatments involve one or more mild treatments coupled with cortisteriod injections. Finally, alternative methods include acupuncture, massage, application of magnets, tai-chi exercises, and the like.

However, none of the above treatments have produced uniformly positive results. While some treatments may alleviate the symptoms of carpal tunnel syndrome in individual patients, the symptoms often return when the course of treatment is terminated. Furthermore, one of the main disadvantages of the various treatment approaches is that they must be delivered by a healthcare provider such as a physician or a physical or occupational therapist. This adds a significant level of inconvenience to the patient who must allocate time to visit the healthcare provider for injections and/or physical therapy. Medications that are used to provide relieve from the pain and discomfort caused by carpal tunnel syndrome also suffer from a number of disadvantages. For example, certain medications have undesirable side effects or interactions with the patient's other medications, if any.

As a result, a number of techniques for treating carpal tunnel syndrome that address at least some of the above problems have been developed over the years. Some merely maintain the patient's hand in a neutral position (such as the device disclosed in U.S. Pat. No. 5,014,689) to prevent the symptoms from worsening. Another approach involved mechanical stretching of the carpal ligament, as disclosed in U.S. Pat. No. 5,256,136. Yet another series of techniques advocated placement of a compression bracelet on the forearm (U.S. Pat. No. 5,441,058), or on the wrist (U.S. Pat. No. 5,468,220) to apply a predetermined pressure on certain portions of the forearm, or wrist, respectively, in order to widen the carpal tunnel and thus provide relief to the patient suffering from carpal tunnel syndrome.

However, the above-described previously known devices suffer from a crucial disadvantage. Application of pressure to different portions of the forearm and/or the wrist only has a minimal effect on widening the carpal tunnel, and may only provide temporary relief from carpal tunnel syndrome rather than eliminating or suppressing the condition.

Further development in the area of mechanical treatment of carpal tunnel syndrome continued, and eventually resulted in discovery of the Porrata principle, disclosed in the commonly assigned U.S. Pat. No. 6,146,347 to Humberto Porrata, that provides a novel and advantageous device and method for treating carpal tunnel syndrome that solve the problems posed by previously known devices and techniques. Most importantly, research conducted in conjunction with development of the Porrata device, has shown that carpal tunnel syndrome may be treated with great effectiveness by precise controlled transverse stretching of the carpal ligament and the flexor retinaculum. The U.S. Pat. No. 6,146,347 patent disclosed a splint-like device that fit over the patient's hand and a portion of the wrist. The device included rigid sections for contacting the thenar and hypothenar portions of the hand and a selectable active pressure source that, when actuated, applied pressure to the dorsal portion of the patient's hand opposed by the forces delivered by the thenar and hypothenar sections of the device in such a manner, as to transversely stretch the carpal ligament and the flexor retinaculum in a comfortable and controlled manner.

Nevertheless, the device of the U.S. Pat. No. 6,146,347 patent is susceptible to improvement. First, because of its construction it generally must be fabricated in different sizes to fit various patients, and patients with unusual hand sized or shapes may need custom-fabricated devices. Second, it generally requires an active adjustable pressure source such as a bladder and pump combination for delivering pressure to the dorsal portion of the hand.

It would thus be desirable to provide an apparatus and method for treating carpal tunnel syndrome by transversely stretching the carpal ligament and the flexor retinaculum of a patient's hand in a comfortable and controlled manner. It would further be desirable to provide an apparatus and method for treating carpal tunnel syndrome embodied in a device that is dynamically adaptable to patients of various physical characteristics. It would also be desirable to provide an apparatus and method for treating carpal tunnel syndrome embodied in a device that is easy and inexpensive to manufacture.

SUMMARY OF THE INVENTION

The apparatus and method of the present invention advantageously overcome the problems and drawbacks of previously known approaches for treating carpal tunnel syndrome. Similarly to the device disclosed in the commonly assigned U.S. Pat. No. 6,146,347 which is hereby incorporated by reference in its entirety, the main objective of the present invention is to apply the Porrata principle to transversely stretch the carpal ligament and the flexor retinaculum, as well as the superficial structures and muscles of the hand, in a safe manner under precise control of the patient or a healthcare professional. However, the apparatus and method of the present invention enable the Porrata principle to be implemented in a device that may be readily used by patients with any size or shape hands. Furthermore, the inventive apparatus is very simple and inexpensive to manufacture.

Controlled and monitored use of the inventive apparatus dynamically treats carpal tunnel syndrome through the active application of pressure to large portions of the palm of the hand (in the thenar and hypothenar areas) while at the same time retaining and leveraging a large portion of the dorsum of the hand, in essence providing pressure in the opposite direction. This procedure transversely stretches the carpal ligament, the flexor retinaculum, and superficial structures and muscles of the hand in the palmar aspect of the hand, in a readily, safely controllable and comfortable manner.

Considering that the constitutions of the carpal ligament and the flexor retinaculum are soft tissue composed of collagen and elastin, stretching the carpal ligament and the flexor retinaculum is effective for decreasing compression on the median nerve by increasing the diameter of the tunnel and decreasing the rigidity of the retinaculum and the carpal ligament, thus alleviating the symptoms of carpal tunnel syndrome.

Various embodiments of the inventive apparatus commonly include a housing for receiving the hypothenar portion of the patient's hand with an open side portion adapted and configured to contact and retain the hypothenar region of the patient's hand with an upper edge of the housing extending along a central longitudinal dorsal portion of the hand, while a flexible resilient strap is wrapped around the thenar portion of the hand (i.e. around the thumb area) in such a manner, as to pull the thenar portion of the hand upward with the upper edge of the housing serving as a fulcrum around which the thenar and hypothenar portions of the hand are bent. The strap is then secured to itself or to the housing to keep the thenar and hypothenar portions pulled apart during the course of treatment.

Accordingly, the inventive apparatus is inexpensive and readily usable by any patient to prevent progression of carpal tunnel syndrome and to provide relief from symptoms, by increasing the cross sectional area of the carpal tunnel, thus decreasing compression on the median nerve and decreasing the resulting symptoms.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims.

BRIEF DESCRIPTION OF THE DRAWINGS

In the drawings, wherein like reference characters denote like elements throughout the several views.

DETAILED DESCRIPTION OF PREFERRED EMBODIMENTS

The present invention is described with reference to various materials that compose the inventive structures and elements thereof, and to various devices for selectively applying pressure to specific areas of the hand, by way of example only—it should be understood that the apparatus and method of the present invention may be utilized with any materials or selective pressure sources having properties similar to those described in the exemplary embodiments, without departing from the spirit of the invention.

The essence of the Porrata approach, disclosed and described in greater detail in the above-incorporated U.S. Pat. No. 6,146,347, involves applying pressure to a portion of the top surface of the hand (i.e., the central dorsal region), while at the same time applying opposing pressure to the thenar and hypothenar regions of the palm. The apparatus and method of the present invention advantageously implement the Porrata principle in a simple-to-use device that works equally well with different hand shapes and sizes.

Figure 1:
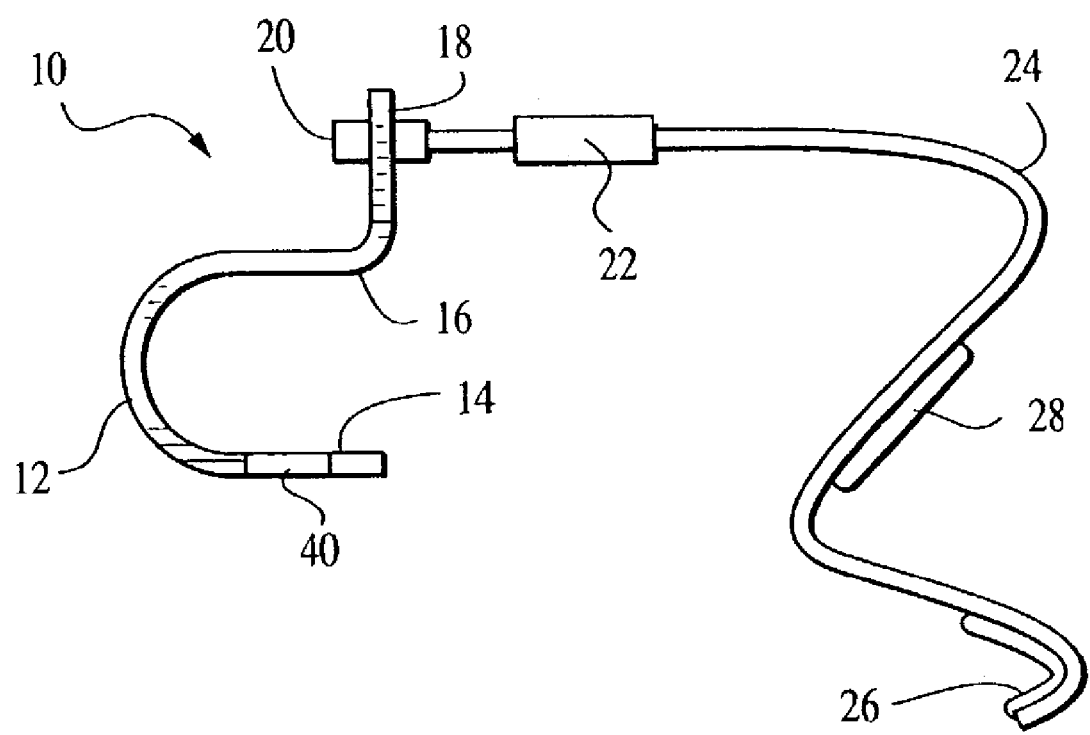
FIG. 1 is a cross section view of a first embodiment of the inventive apparatus for treating carpal tunnel syndrome.
Figure 2:
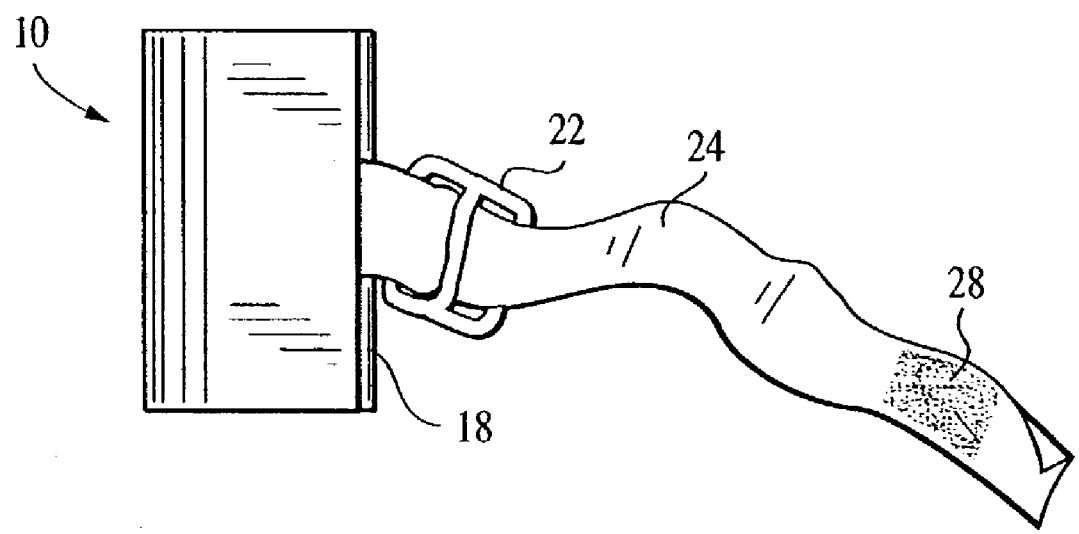
FIG. 2 is a top view of the first embodiment of the inventive apparatus for treating carpal tunnel syndrome of FIG. 1.

Referring now to FIGS. 1-2, a first embodiment of an inventive apparatus 10 is shown. The apparatus 10 includes a housing 12 with a first support section 14 for retaining the hypothenar region of the hand, and a top edge 16 disposed generally along the longitudinal central dorsal portion of the hand. The housing 2 may be composed of a rigid material such as metal, hard plastic or wood, or a resilient material such as fiberglass or resilient plastic, or a combination thereof. Optionally, the housing 12 may include a plurality of ventilation openings (not shown) to provide ventilation to the patient's hand during the operation of the apparatus 10. A fulcrum 18 may be an upraised member substantially perpendicular to the dorsal region of the hand extending from or near the top edge 16. The fulcrum 18 may be a different, separate element from or near the housing 12, it may be an extension thereof, or it may be integral thereof. A flexible resilient strap 24 is attached to the fulcrum 18 via an attachment device 20. The strap 24 may be composed of any resilient material such as nylon webbing, leather, rubber, or any other synthetic or natural resilient flexible material. The strap 24 may optionally include a length adjustment device 22, such as a buckle. The strap 23 also includes optional releasable attachment connectors 26, 26, such as a hook and loop mechanism, a snap and the like (optionally only one such connector may be included).

Figure 3:
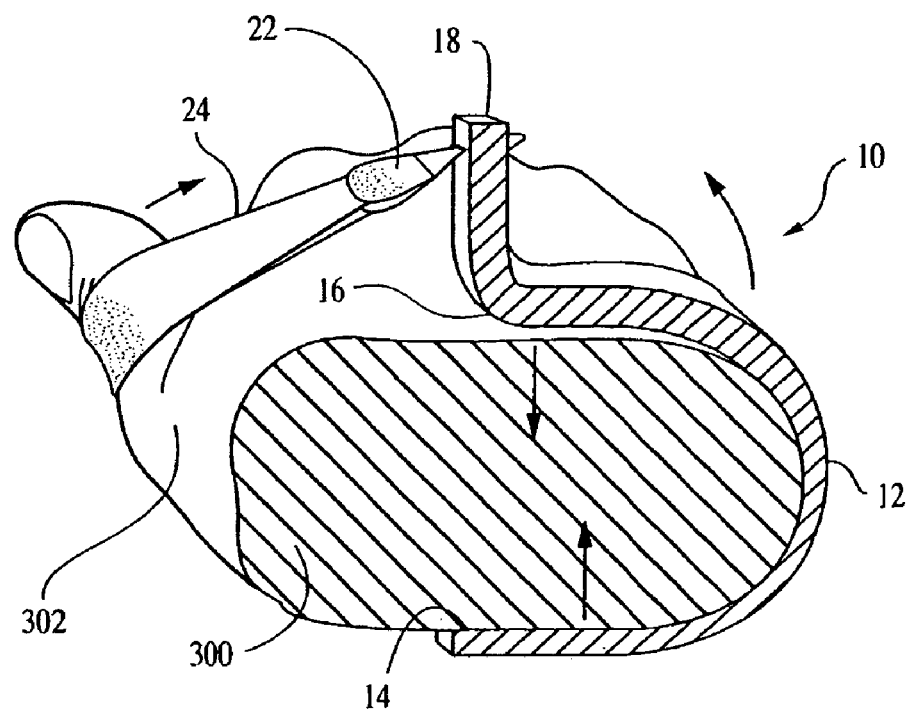
FIG. 3 is a cross section view of the first embodiment of the inventive apparatus for treating carpal tunnel syndrome of FIG. 1, during utilization.

Referring now to FIG. 3, the apparatus 10 is shown during its operation. A person places their hand 300 into the housing 12, such that the hypothenar region of the palm contacts the support section 14 and the edge 16 is disposed along the central dorsal portion of the hand 300. The strap 24 is then tightly wrapped around the thenar region 302 of the hand 300, and pulled towards the fulcrum 18. This tension or pulling action exerts a first upward force on the thenar region of the hand opposed by the downward force exerted by the fulcrum 18 on the central longitudinal dorsal region of the hand through the edge 16, and approximately parallel to a corresponding second upward force exerted by the support section 14 on the hypothenar region of the hand. The strap 24 is then secured to itself by a knot or via the attachment connectors 26, 28 to maintain tension therein sufficient to maintain the first and second upward forces and the downward force. The downward force is balanced and opposed by said first and said second upward forces causing the carpal bones of the hand to separate to transversely stretch a carpal ligament and a flexor retinaculum of the hand, thus implementing the Porrata principle to widen the carpal canal and provide treatment of carpal tunnel syndrome to the patient.

FIG. 1 also shows that the apparatus 10 may also include an electronic device 40 that includes a laser or similar device adapted to specifically denature the proteins that make up the ligaments in the body, thus making it easier to stretch the ligaments. The electronic device 40 is preferably aligned with the flexor retinaculum or carpal ligament as the hand is placed in the apparatus 10. The electronic device 40 may also include conventional sensors to measure the amount of stretching of the flexor retinaculum or carpal ligament through, e.g., tension measurements or displacement of carpal bones.

Figure 4:
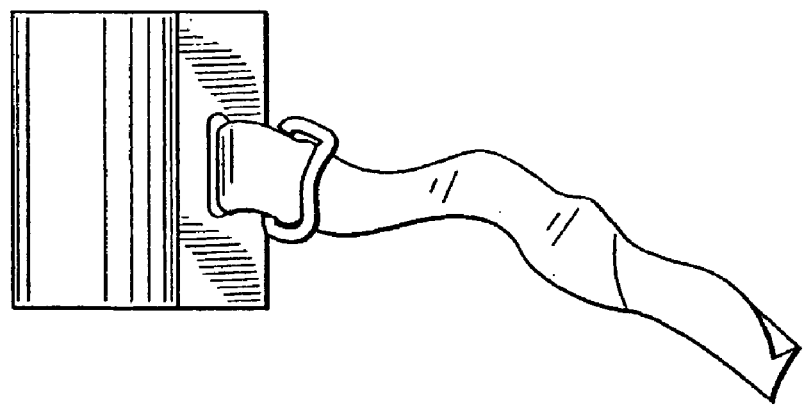
FIGS. 4-6 are various views of an exemplary implementation of the inventive apparatus for treating carpal tunnel syndrome of FIG. 1.
Figure 5:
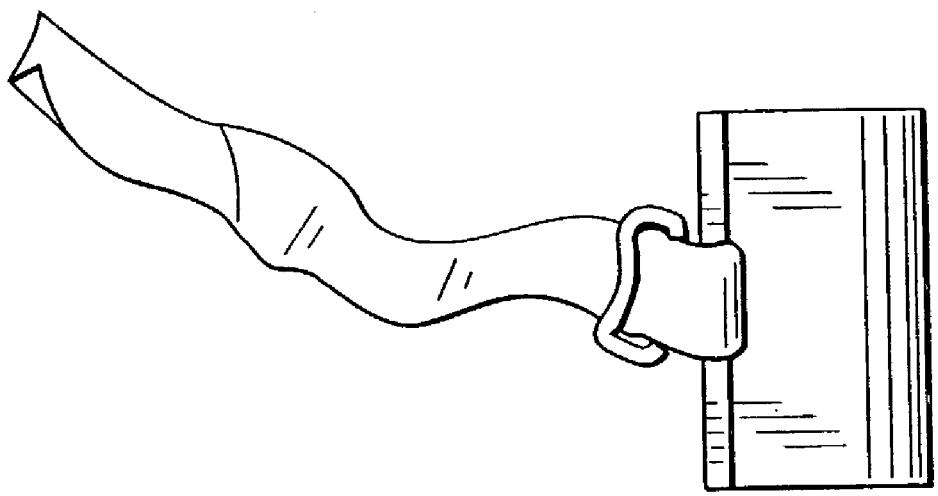
Figure 6:
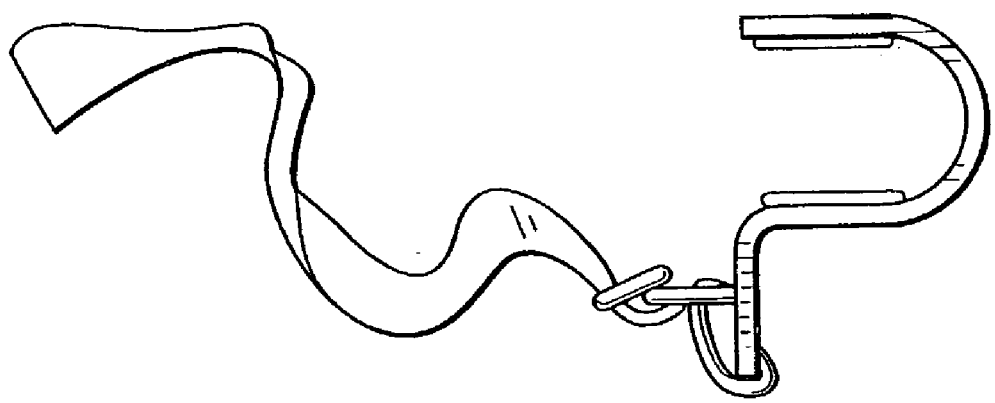
Figure 7:
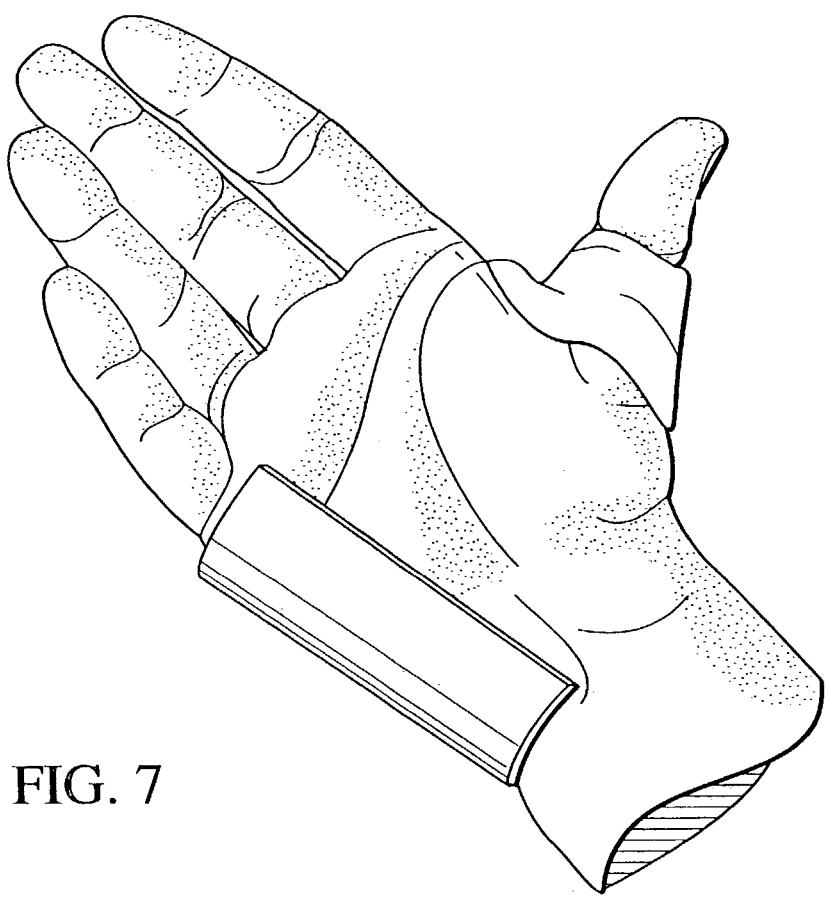
FIGS. 7-9 are various views of an exemplary implementation of the inventive apparatus for treating carpal tunnel syndrome of FIG. 1, during utilization by a patient.
Figure 8:
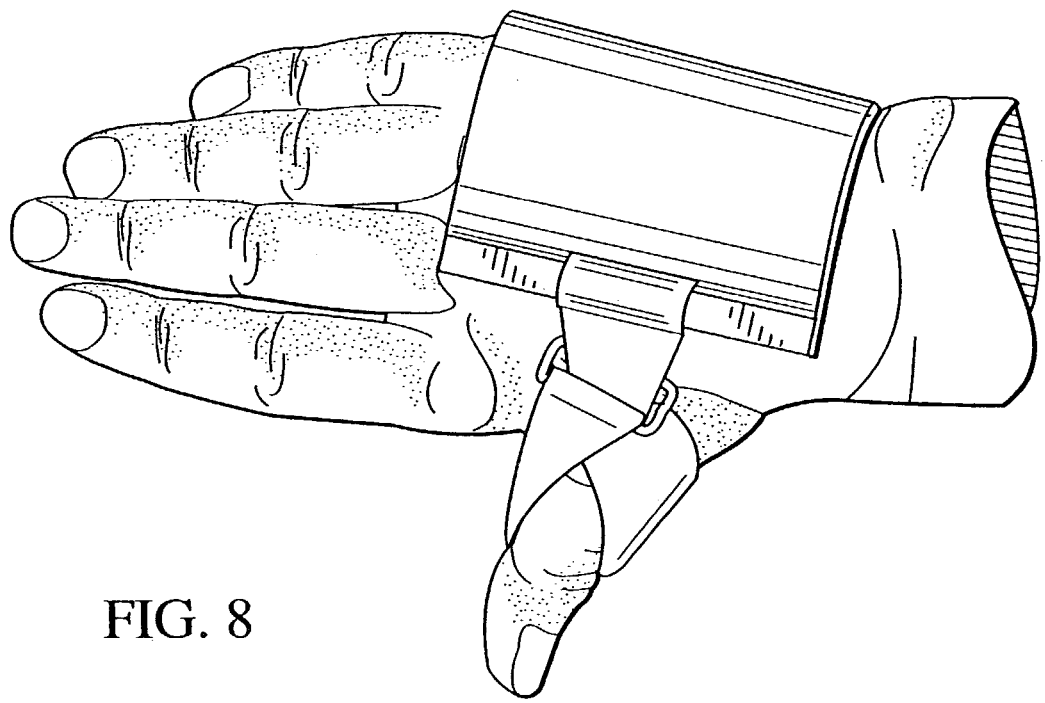
Figure 9:
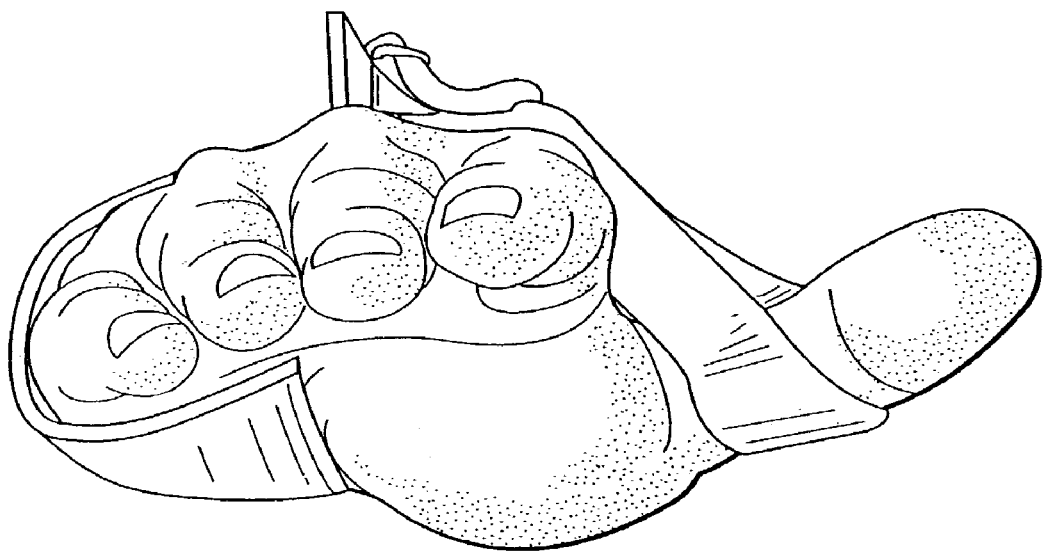

Referring now to FIGS. 4-6, various views of an exemplary embodiment of the apparatus 10 is shown. Referring now to FIGS. 7-9, various views of the exemplary embodiment of the apparatus 10 of FIGS. 4-6 are shown during utilization of the apparatus 10 by a patient.

Figure 10:
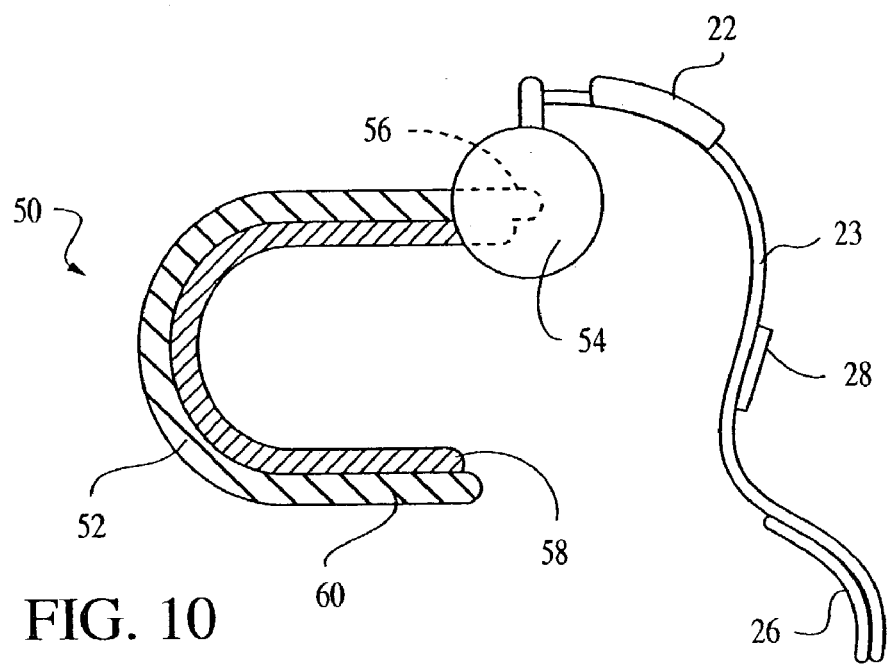
FIG. 10 is a cross section view of a second embodiment of the inventive apparatus for treating carpal tunnel syndrome.

Referring now to FIG. 10, a second embodiment of the apparatus 10 is shown as an apparatus 50. The apparatus 50 operates similarly to the apparatus 10, except that the fulcrum 18 is implemented as a pressure member 54 encompassing an edge 56 to improve patient's comfort. The apparatus 50 also includes an optional resilient lining 58 along the inner surface of a housing 52. The lining 58 may be composed of any resilient material including but not limited to: soft plastic, silicone gel, padding, foam, spring elements, and at least one fluid or air-filled bladder. Optionally, the lining 58 may be disposed only along a support section 60 rather than covering the entire interior of the housing 52. The strap 24 may optionally include a length adjustment device 22, such as a buckle. The strap 23 also includes optional releasable attachment connectors 26, 26, such as a hook and loop mechanism, a snap and the like (optionally only one such connector may be included).

Figure 11:
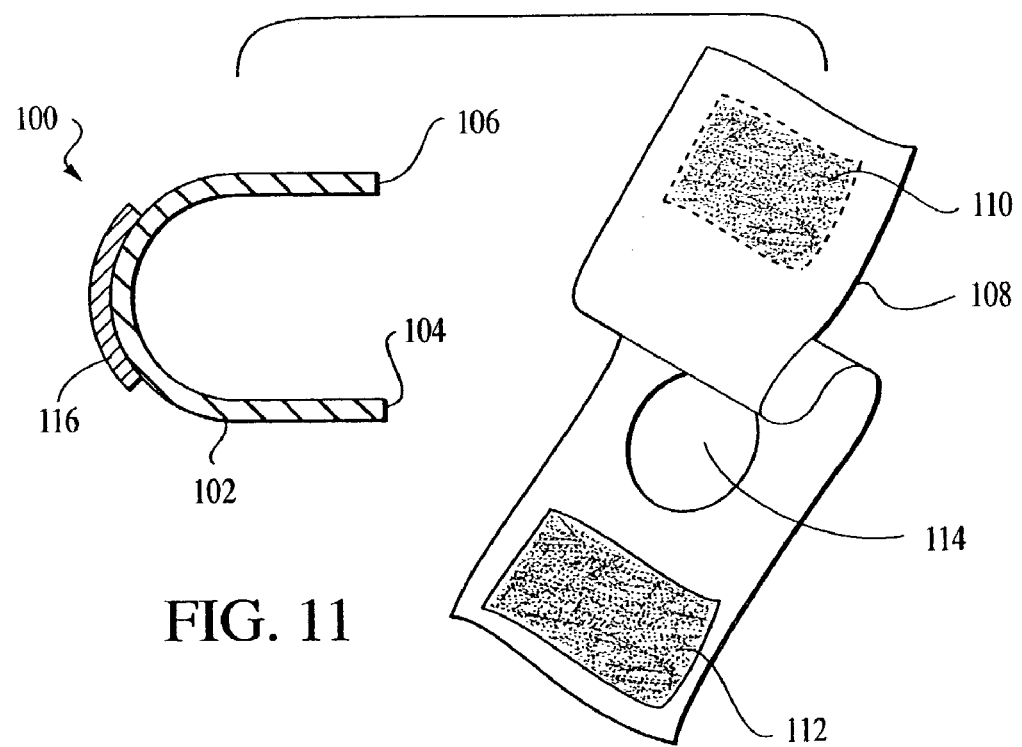
FIG. 11 is a cross section view of a third embodiment of the inventive apparatus for treating carpal tunnel syndrome.
Figure 12:
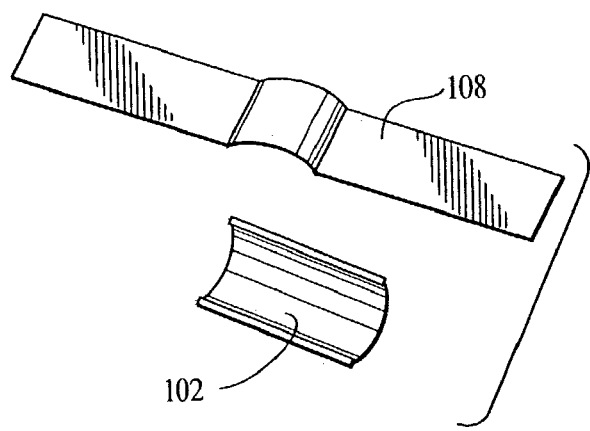
FIG. 12 is a top isometric view of the third embodiment of the inventive apparatus for treating carpal tunnel syndrome of FIG. 11.
Figure 13:
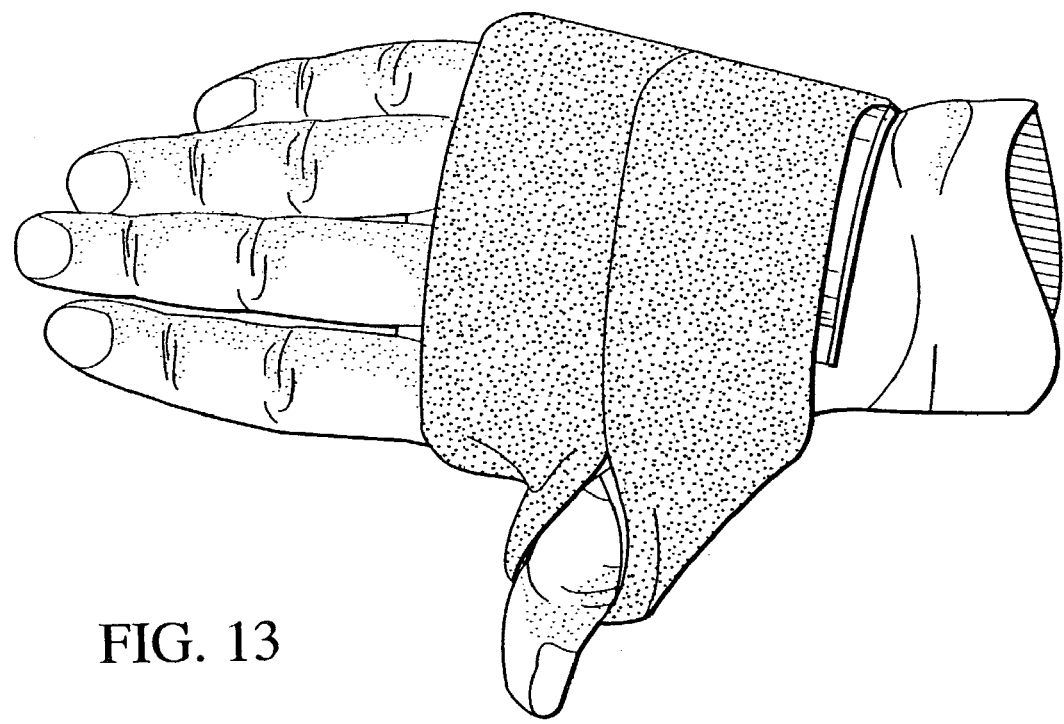
FIG. 13 illustrates an exemplary implementation of the inventive apparatus for treating carpal tunnel syndrome of FIG. 11, during utilization by a patient.

Referring now to FIG. 11, a third embodiment of the inventive apparatus is shown as an apparatus 100. The apparatus 100 includes a housing 102 with a first support section 104 for retaining the hypothenar region of the hand, and a top edge 106 disposed generally along the longitudinal central dorsal portion of the hand when the hand is inserted into the housing 102. The housing 102 may be composed of a rigid material such as metal, hard plastic or wood, or a resilient material such as fiberglass or resilient plastic, or a combination thereof. The housing 102 also includes a releasable connector 116 on its outer surface, such as a hook and loop mechanism, a snap or the like. The releasable connector 116 may be singular, or it may be split up into two or more separate pieces. A separate flexible resilient strap 108 is provided. The strap 108 may be composed of any resilient material such as nylon webbing, leather, rubber, or from any other synthetic or natural resilient flexible material. The strap 108 includes releasable attachment connectors 110, 112 (optionally only one such connector may be included but extended along the length of one or both of the surfaces of the strap 108), for releasable attachment to the releasable connector 116. For example, connector 116 may be hook material while connectors 110, 112 may be corresponding loop material. The strap 108 may include an optional hole 114 for receiving the thumb. The apparatus 100 operates similarly to apparatus 10 of FIG. 1, in that one end of the strap 108 is attached to the housing 102, while the rest of the strap is wrapped around the thenar region of the hand, pulled toward the edge 106, and then attached to the housing 102 via the connector 116 with sufficient tension to implement the Porrata principle. Referring now to FIG. 12, a side isometric view of an exemplary embodiment of the apparatus 100 is shown. FIG. 13 illustrates an exemplary embodiment of the apparatus 100 of FIG. 12 during utilization of the apparatus 100 by a patient.

Figure 14:
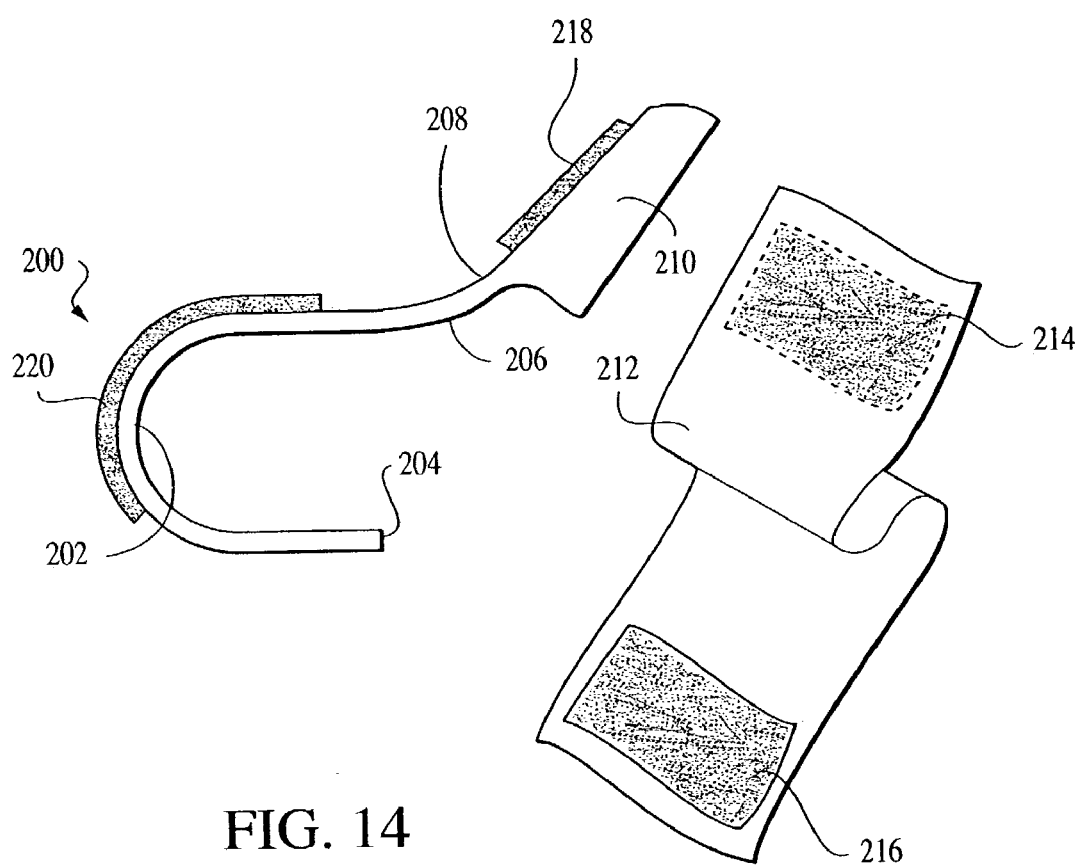
FIG. 14 is a cross section view of a fourth embodiment of the inventive apparatus for treating carpal tunnel syndrome.
Figure 15:
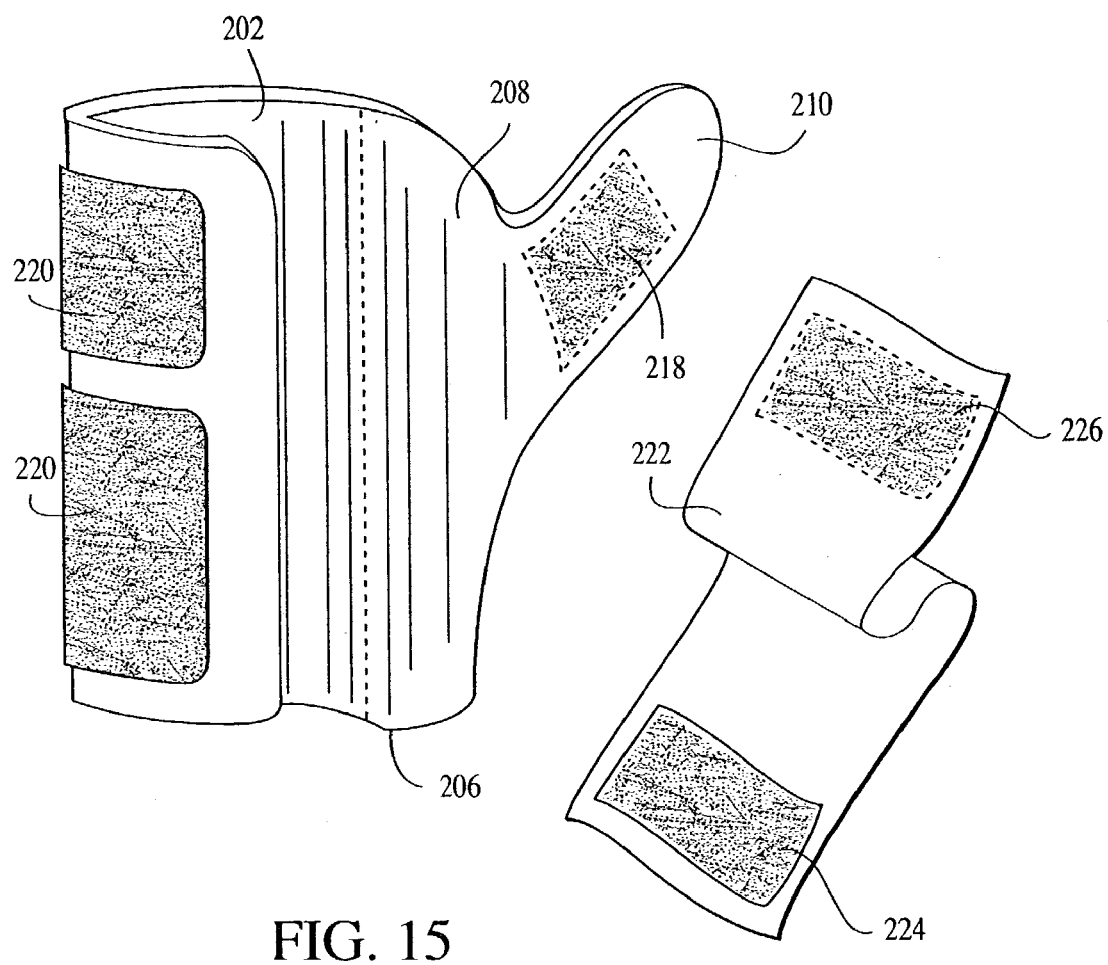
FIG. 15 is a bottom view of the fourth embodiment of the inventive apparatus for treating carpal tunnel syndrome of FIG. 14.

Referring now to FIGS. 14-15, a fourth embodiment of the inventive apparatus is shown as an apparatus 200. The apparatus 200 includes a housing 202 with a first support section 204 for retaining the hypothenar region of the hand, a top edge 206 disposed generally along the longitudinal central dorsal portion of the hand when the hand is inserted into the housing 202, and a second support section 208 extending from the edge 206 at a predetermined angle to the first support section 204. The second support section 208 may include an optional thumb support section 210. The housing 202 may be composed of a rigid material, such as metal, hard plastic or wood, or a resilient material such as fiberglass or resilient plastic, or a combination thereof. The housing 202 also includes a first releasable connector 218 on an outer portion of the thumb support section 210, and a second releasable connector 220 on its outer surface between the first support section 204 and the edge 206. The exact positions of the connectors 218, 220, and the number of connectors used, are selected as a matter of design choice and may be changed without departing from the spirit of the invention.

A flexible resilient strap 212 is provided for use in conjunction with the housing 202. The strap 212 may be composed of any resilient material such as nylon webbing, leather, rubber, or any other synthetic or natural resilient flexible material. The strap 212 includes releasable attachment connectors 214, 216 (optionally only one such connector may be included but extended along the length of one or both of the surfaces of the strap 212) for releasable attachment to the releasable connectors 218, 220. For example, connectors 218, 220 may be hook material, while connectors 214, 216 may be corresponding loop material.

Figure 16:
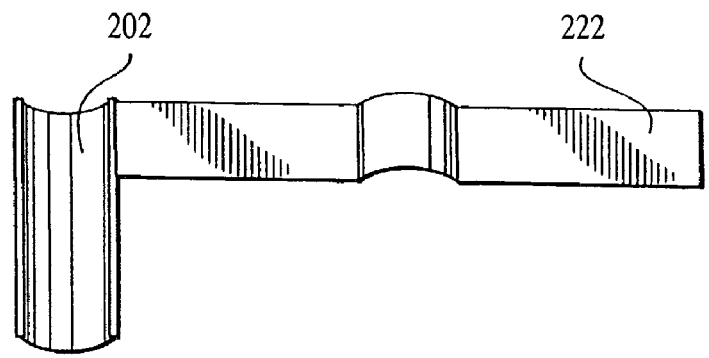
FIG. 16 is a side view of the fourth embodiment of the inventive apparatus for treating carpal tunnel syndrome of FIG. 14.
Figure 17:
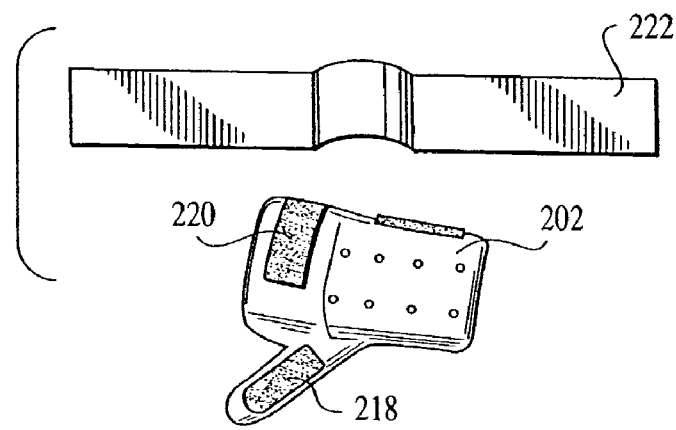
FIG. 17 is a top view of the fourth embodiment of the inventive apparatus for treating carpal tunnel syndrome of FIG. 14.
Figure 18:
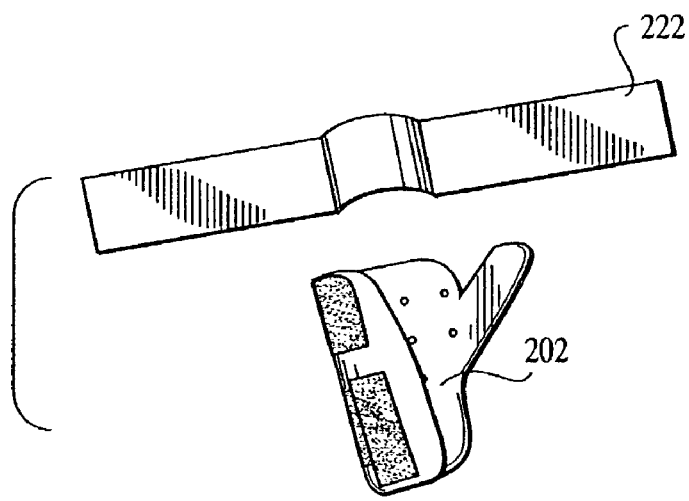
FIG. 18 is a bottom isometric view of the fourth embodiment of the inventive apparatus for treating carpal tunnel syndrome of FIG. 14.
Figure 19:
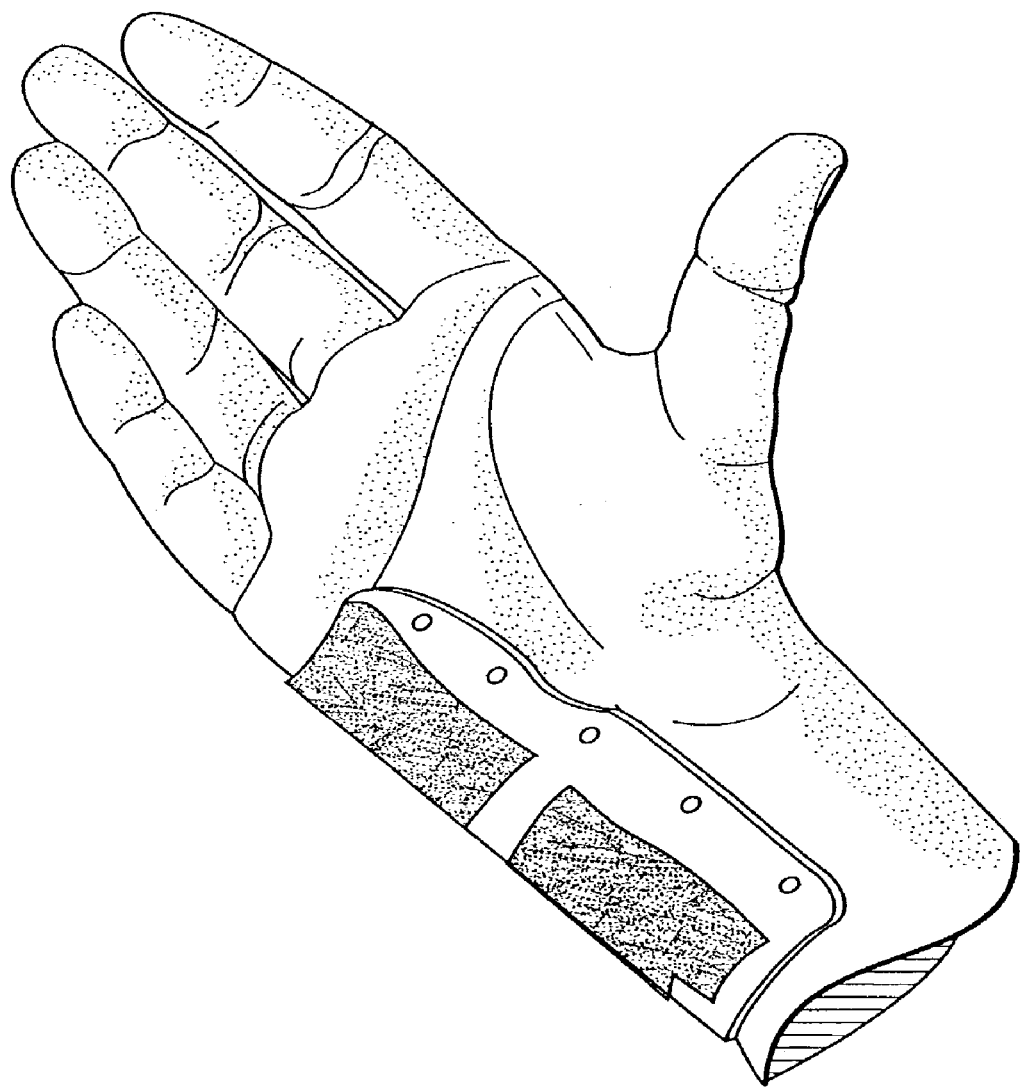
FIGS. 19-21 are various views of an exemplary implementation of the inventive apparatus for treating carpal tunnel syndrome of FIG. 14, during utilization by a patient.
Figure 20:
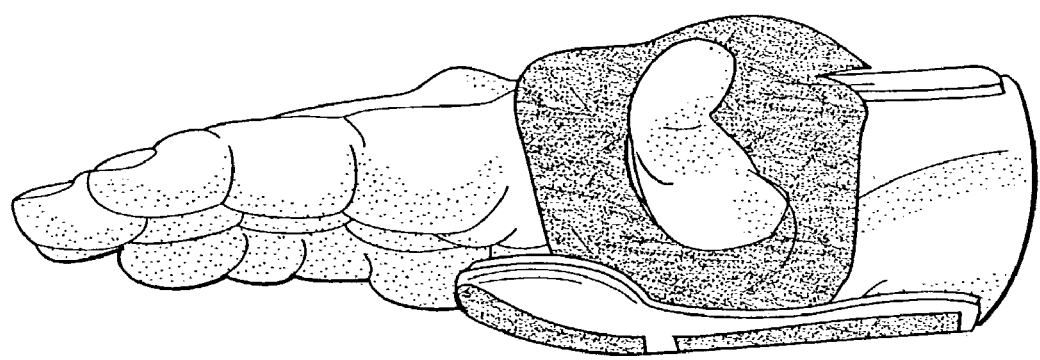
Figure 21:
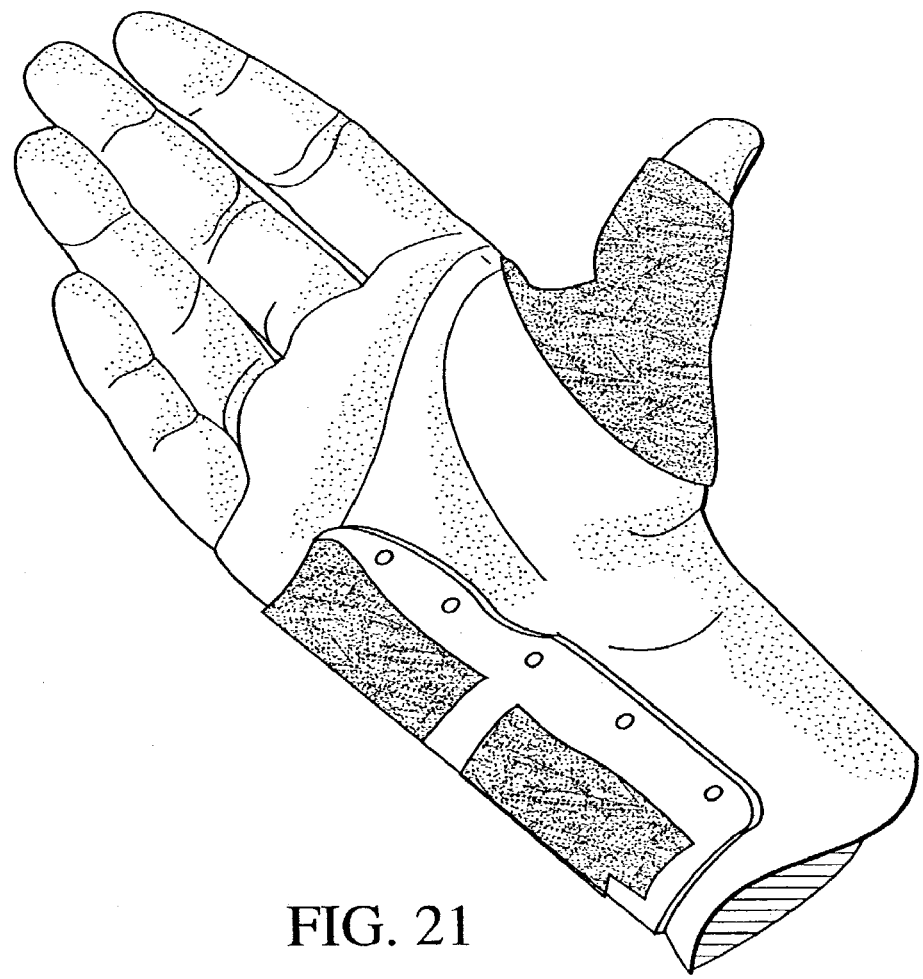

The apparatus 200 operates similarly to apparatus 10 of FIG. 1, in that one end of the strap 212 is attached to the housing 202, while the rest of the strap 212 is wrapped around the thenar region of the hand to pull the hand upward until a top dorsal portion of the hand, corresponding to the thenar region below, is pulled into contact with the second support section 208. The strap 212 is then attached to the housing 202 with sufficient tension to implement the Porrata principle. The connectors 214, 216 on the strap 212, and the connectors 218, 220 on the housing 202, serve to maintain the tension on the strap 212 and thus to maintain the various forces exerted on the thenar, hypothenar and dorsal regions of the hand. Optionally, one portion of the strap 212 may be permanently attached to the housing 202 using a variety of conventional methods. Referring now to FIGS. 16-18, various views of an exemplary embodiment of the apparatus 200 of FIG. 14 are shown. Referring now to FIGS. 19-21, various views of the exemplary embodiment of the apparatus 200 of FIG. 14 are shown during utilization of the apparatus 200 by a patient.

It should be noted that the individual elements shown in various embodiments of FIGS 1-21 may be readily utilized in different embodiments or mixed without departing from the spirit of the invention. For example, the resilient lining 58 of the apparatus 50 of FIG. 10 may be utilized in the apparatus 10 of FIG. 1, the apparatus 100 of FIG. 11 or the apparatus 200 of FIG. 14. Furthermore, while cross sections of the various embodiment of the inventive apparatus are shown to be of semi-elliptical in shape, the cross section of the inventive apparatus may comprise any other geometrical shape without departing from the spirit of the invention.

Thus, while there have been shown and described and pointed out fundamental novel features of the invention as applied to preferred embodiments thereof, it will be understood that various omissions and substitutions and changes in the form and details of the devices and methods illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. It is the intention, therefore, to be limited only as indicated by the scope of the claims appended hereto.

We claim:

1. An apparatus for treating carpal tunnel syndrome in a person's hand, the hand having a longitudinal axis, a palmar aspect with thenar and hypothenar regions and a central dorsal region opposed to the palmar aspect, the apparatus comprising a housing having a first lower support section, a curved section that includes an open interior region, extending between said first lower surface and a top portion, said top portion comprising a first edge, a fulcrum extending upwardly from said first edge, said open interior region adapted to receive the hypothenar portion of the hand, said first edge is positioned along the longitudinal axis of the central dorsal region of the hand, said first lower support section contacts at least a portion of the hypothenar region of the palmar aspect of the hand, a tension means for retaining the thenar region of the hand and for applying a first upward force on the thenar region of the hand opposed by a downward force exerted by said first edge on the central dorsal region of the hand, wherein a second upward force is exerted by the first support section on the hypothenar region of the palmar aspect of the hand in response to the first upward force is exerted, such that the downward force is balanced and opposed by the first and second upward forces, wherein said downward force and said first and second upward forces causes carpal bones of the hand to separate to transversely stretch a carpal ligament and flexor retinaculum of the hand, said first support section having an electronic device attached to a top surface thereof, said electronic device further comprising a sensor that measures the amount of stretching of the flexor retinaculum or the carpal tunnel ligaments.

2. The apparatus of claim 1, wherein said tension means comprises an elongated resilient strap having a first end and a second end, wherein the strap is wrapped around the thenar region of the hand; first securing means for securing a first end of the housing to the hand, second securing means for securing the second end to said housing after said strap is wrapped around the thenar region with sufficient tension to exert the first upward force on the thenar region of the hand in an opposite direction to the downward force exerted by the first edge.

3. The apparatus of claim 2, wherein the strap comprises a hole sized and configured to receive a thumb to improve the precision of application of said first upward force to the thenar region of the hand.

4. The apparatus of claim 2, wherein said first securing means comprises first releasable securing means and wherein said second securing means comprises second releasable securing means.

5. The apparatus of claim 1, wherein the housing further comprises a third securing means for securing one portion of the tension means to said fulcrum and a fourth securing means for securing another portion of the tension means to the fulcrum.

6. The apparatus of claim 5, wherein the fourth securing means comprises a third releasable securing means.

7. The apparatus of claim 1, wherein the housing further comprises a second support portion extending from the first edge at a predetermined angle to the dorsal region of the hand, such that when the tension means is applied to the thenar region, a top portion of the hand, corresponding to the thenar region below, is pulled into contact with the second support portion causing the and to bend around the edge.

8. The apparatus of claim 7, wherein the second support portion includes a third support portion for supporting the thumb.

9. The apparatus of claim 7, wherein the housing comprise a fourth support portion that extends at least from the first and second support portions to support the wrist.

10. The apparatus for claim 1, wherein the electronic device further comprises a laser adapted to denature proteins forming the flexor retinaculum and carpal ligament.

11. An apparatus for treating carpal tunnel syndrome in a person's hand, the hand having a longitudinal axis, a palmar aspect with thenar and hypothenar regions, and a central dorsal region opposed to the palmar aspect, the apparatus comprising a substantially U-shaped housing adapted to fit the thenar and hypothenar regions of the hand, a resilient lining attached to an interior surface of said housing, a circular pressure member attached to said housing, said circular pressure member is a fulcrum, said circular pressure member encompasses an edge of said housing, to apply pressure to the central longitudinal dorsal region of the hand to provide treatment for carpal tunnel syndrome and a flexible tension means extending outwardly from said housing, said tension means having an adjustment means thereon for adjusting the length of said tension means.

12. A method for treating carpal tunnel syndrome in a person's hand, the hand having a longitudinal axis, a palmar aspect with thenar and hypothenar regions and a central dorsal region opposed to the palmar aspect, the method comprising the steps of placing a hand in a housing, wherein the hypothenar region of the palm contacts a support section of said housing, disposing an edge of said housing along the central dorsal portion of the hand, wrapping a tension means tightly around the thenar region of the hand and pulling the tension means towards a fulcrum that is located on said housing, using the tension means to exert a first upward force on the thenar region of the hand, said upward force is opposed by a downward force that is exerted by the fulcrum on the central longitudinal dorsal region of the hand through the edge and substantially parallel to a corresponding second upward force exerted by the support section on the hypothenar region of the hand, securing the tension means to itself using connectors to maintain tension sufficient enough to maintain the first and second upward forces and the downward force, balancing the downward force to oppose the first and second upward forces to cause the carpal bones of the hand to separate to transversely stretch a carpal tunnel ligament and flexor retinaculum of the hand, said housing having a sensor means located on the support section, using said sensor means to measure the amount of stretching of the flexor retinaculum or carpal ligaments.

* * * * *